United States Patent [19]

Yamaguchi et al.

[11] Patent Number: 4,485,823
[45] Date of Patent: Dec. 4, 1984

[54] APPARATUS FOR DIAGNOSING ENVIRONMENTAL TISSUE OF TOOTH

[75] Inventors: Akiya Yamaguchi, Tokyo, Japan; Marvin M. Stark; Kenneth B. Soelberg, both of San Francisco, Calif.

[73] Assignee: Sankin Industry Co., Ltd., Osaka, Japan

[21] Appl. No.: 293,502

[22] Filed: Aug. 17, 1981

[30] Foreign Application Priority Data

Dec. 27, 1980 [JP] Japan ............................ 55-189189

[51] Int. Cl.³ ............................................. A61B 5/05
[52] U.S. Cl. ................................. 128/739; 128/777; 128/776
[58] Field of Search ........ 128/774, 776, 777, 739–740, 128/773, 737, 741, 746; 33/174 D; 73/658, 661, 862.59, DIG. 1

[56] References Cited

U.S. PATENT DOCUMENTS 3,091,234  5/1963  Jerger ................................. 128/746
3,094,115  6/1963  Polin ................................. 128/776 X
3,653,373  4/1972  Batterman ...................... 128/776 X
3,943,913  3/1976  Johnson ............................. 128/776
4,164,214  8/1979  Stark et al. ........................ 128/741
4,192,321  3/1980  Korber et al. ..................... 128/776
4,340,069  7/1982  Yeaple ............................... 128/776

FOREIGN PATENT DOCUMENTS 1126264  11/1956  France ............................... 128/741

Primary Examiner—Lee S. Cohen
Assistant Examiner—Angela D. Sykes
Attorney, Agent, or Firm—Lothrop & West

[57] ABSTRACT

An apparatus for diagnosing the environmental tissue of teeth, which has an electro-mechanical oscillation converter for converting the electric oscillation output from an electric oscillation output generation circuit into mechanical oscillation, a probe connected to the converter to be brought into contact with a patient's tooth for applying the mechanical oscillation from the converter to the tooth, and patient's responding means for actuation by the patient when he detects the sense threshold of the mechanical oscillation applied through the probe to the patient's tooth. Thus, a dentist can scientifically diagnose the health of the tissue of the patient's teeth as distinguished from the diseased part without visual examination nor palpation by the dentist.

2 Claims, 3 Drawing Figures

APPARATUS FOR DIAGNOSING ENVIRONMENTAL TISSUE OF TOOTH

BACKGROUND OF THE INVENTION

This invention relates to a dental diagnostic apparatus and, more particularly, to an apparatus for diagnosing the environmental or peripheral tissue of teeth by numerically identifying the degree of health of the patient's teeth.

In case a patient has a disease in the environmental tissue of his teeth as an example, a dentist normally diagnoses degree of health of the teeth by visually examining or by investigating the patient's diseased portions by palpation and noting the basis of the patient's reactions. There is no other effective scientific diagnosing means than this direct diagnosis.

The dentist has had difficulty accurately diagnosing the degree of health of the general peripheral tissue of the patient's teeth, because it was difficult for the dentist to identify the degree of health of the environmental tissue of the patient's teeth even by visual examination or on palpation as described above, and so it is desired to disclose a scientific diagnostic aid for exactly identifying the patient's degree of health of the peripheral tissue of the patient's teeth.

SUMMARY OF THE INVENTION

Accordingly, a primary object of this invention is to provide an apparatus for diagnosing the environmental tissue of teeth which can scientifically diagnose the degree of health of the environmental tissue of the patient's teeth.

Another object of this invention is to provide an apparatus for diagnosing the environmental tissue of teeth which can diagnose the degree of health of the peripheral tissue of the patient's teeth without visual examination or palpation by the dentist.

Yet another object of this invention is to provide an apparatus for diagnosing the environmental tissue of teeth which can numerically identify the degree of health of the peripheral tissue of the patient's teeth by identifying the diseased part via the sensed frequency band or amplitude of mechanical oscillation transmitted through the patient's tissue so as to enable an optimum therapy for treatment thereafter of the diseased part of the peripheral tissue of the patient's teeth.

A further object of this invention is to provide an apparatus for diagnosing the environmental tissue of teeth which can also exactly diagnose intraperitoneally the diseased part.

Still another object of this invention is to provide an apparatus for diagnosing the environmental tissue of teeth which does not confuse the sensatory threshold felt by a patient by mechanical oscillation given to the patient's tissue cells with the patient's auditory sensation caused by the sounds of the same frequency transmitted to him through the surrounding air.

The above and other related objects and features of the invention will be apparent from a reading of the following description of the disclosure found in the accompanying drawings and the novelty thereof pointed out in the appended claims.

DESCRIPTION OF THE PREFERRED EMBODIMENT

Figure 1:
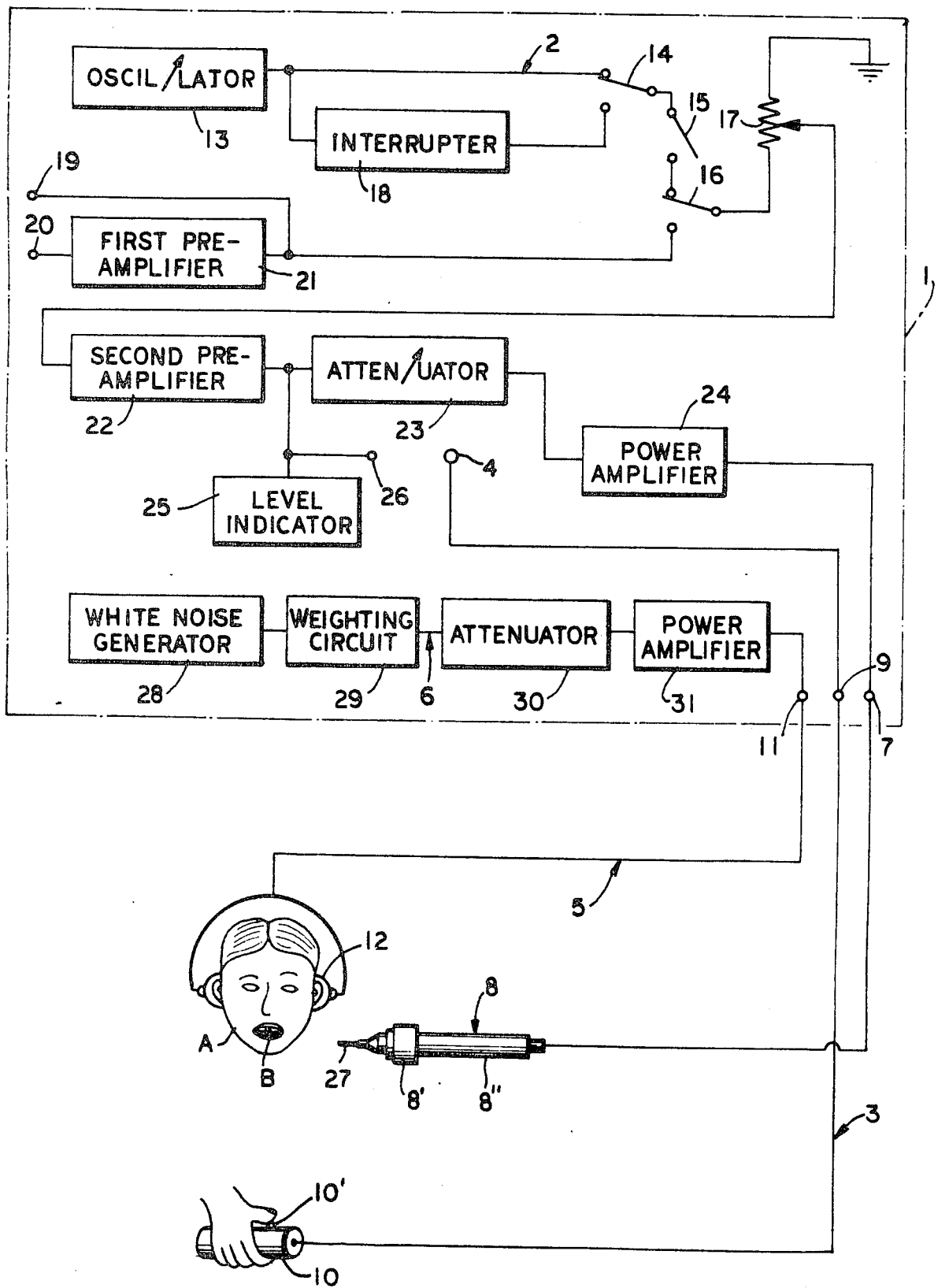
FIG. 1 is a block diagram of one preferred embodiment of an apparatus constructed according to this invention.
Figure 2:
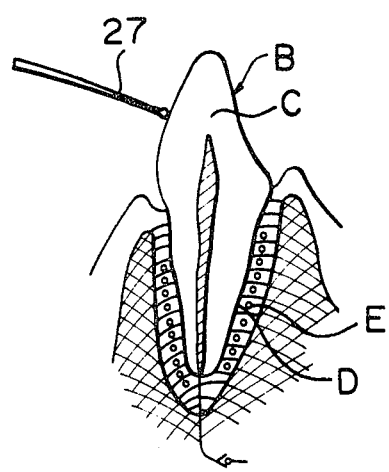
FIG. 2 is a partial side cross sectional view of an oscillation probe of an apparatus of this invention in contact with the patient's tooth in diagnosing the peripheral tissue of the tooth.

Referring now to the drawings, particularly to FIG. 1 showing one preferred embodiment of the apparatus for diagnosing the environmental tissue of teeth constructed according to this invention, wherein like reference numerals designate the same parts in the following views, a dental diagnostic device generally designated by reference numeral 1 comprises an electric oscillation output generation circuit 2, a patient's responding means or unit 3, a response display unit 4 for the patient's responding unit 3, an acoustic shielding means or unit 5 and an acoustic sound generating electric circuit 6 for the acoustic shielding unit 5, all internally contained therein. The patient's responding unit 3 is constructed by connecting an electro-mechanical oscillation converter 8, which will be hereinafter described in greater detail, to an output terminal of the electric oscillation output generation circuit 2 and connecting a manual switch 10 to a display terminal 9 of the response display unit 4. The acoustic shielding unit 5 is constructed by connecting a headphone 12 to be mounted at the ear of the patient A to a headphone terminal 11 of the acoustic sound generating electric circuit 6.

The electric oscillation output generation circuit 2 in the dental diagnostic device 1 will now be first described in detail. The electric oscillation output generation circuit 2 has a built-in electric oscillator 13, which generates an oscillation of audio frequency, preferably of variable frequency.

The electric oscillator 13 produces at the output the audio frequency signal through a first change-over switch 14, a manual interrupter 15 and a second change-over switch 16 to a level regulator or a potentiometer 17 grounded at one end. Further, the oscillation frequency output signal of the oscillator 13 is fed to the level regulator 17 through an automatic interrupter 18.

Reference numerals 19 and 20 illustrate input terminals to which an external electric oscillator may be connected (not shown). In case that the external electric oscillator has a high output, the output of the external electric oscillator may be connected directly to the terminal 19, which applies the output of the external oscillator through the switch 16 to the level regulator 17, while in case the external oscillator has a low output, the output of the external oscillator is connected to the terminal 20, which applies the output of the external oscillator through a first pre-amplifier 21, and the switch 16 to the level regulator 17.

The level regulator 17 is connected by a control arm through a second pre-amplifier 22, an attenuator 23 and an electric power amplifier 24 to the output terminal 7. A level indicator 25 is connected between the second pre-amplifier 22 and the attenuator 23. Reference numeral 26 is a monitor terminal.

The level regulator 17 serves to maintain a constant input signal to the second pre-amplifier 22. The level regulator 17 may be controlled by reading the voltage value of the level indicator 25 to thereby maintain the input signal level to the attenuator 23 suitably at a constant voltage. The attenuator 23 may also be controlled variably, and may be controlled at its constant input signal as desired in amplitude such as by a dial operation or the like.

The electro-mechanical oscillation converter 8 will now be described in detail to be connected to the output terminal 7. The converter 8 may have a size and a weight capable of manual control by a dentist as a vibrator or oscillator. The converter 8 has an oscillation converting unit 8' for converting an electric signal received as an electric oscillation output from the power amplifier 24 into mechanical oscillation or vibration, and a holder 8" provided at one end of the converting unit 8'. The converter 8 also has a stylus-like oscillation probe 27 projected and mounted detachably or replaceably by thread means at the other end of the converting unit 8'. When the probe 27 is brought by manual operation into contact with the surface of a patient's tooth at the tip, it transmits the mechanical oscillation directly to the tooth to be diagnosed.

It is noted that the probe 27 may be made preferably of a hard metal or hard synthetic resin which will not slip but will efficiently transmit the oscillation when making contact with the enameled portion of the crown of a tooth, and may also preferably endure against sterilization treatment and have an insulating property.

The patient's responding unit 3, as shown, is exemplified in the simplest construction, and serves to turn on a pilot lamp as the response display unit 4 in the dental diagnostic device 1 by depressing the push-button 10' of the manual switch 10 held by the patient A. The patient's responding unit 3 may not be limited to this, but may also be instead a buzzer as the response display unit 4 only if the patient A can so express his response to the dentist.

The acoustic sound generating electric circuit 6 for the acoustic shielding unit 5, as exemplified, has a white noise generator 28 for generating a plurality of white noise waves, a weighting circuit 29 connected to the generator 28 for weighting the original amplitude of the white noise generated by the generator 28 to impart unevenness to the amplitude of the white noise, an attenuator 30 for receiving the output of the weighting circuit 29 for attenuating the same, and an electric power amplifier 31 for amplifying the white noise. The white noise adjusted in amplitude suitably by the attenuator 30 is amplified by the power amplifier 31 and is then applied to the headphone 12.

In operation, the headphone 12 is attached to a patient A, the white noise is thus fed to the patient in this manner, and the manual switch 10 is held by the patient. Then, an audio frequency band electric oscillation output is applied from the built-in electric oscillator 13 or an external electric oscillator to the electro-mechanical oscillation converter 8. It is noted that the oscillator or converter 8 may be adjusted to generate the electric output of 150 Hz to 700 Hz in variable frequency, and the output of the converter 8 may be regulated in a range of 0 dB to 60 dB by the attenuator 23.

The converter 8 is adjusted, for example, to generate an electric oscillation output of a suitable frequency such as 350 Hz, and the output voltage level is regulated at a predetermined value by the level regulator or potentiometer 17. Then, the electro-mechanical oscillation converter 8 is manually operated, and the probe 27 is brought into contact with the surface of the tooth B in the mouth of the patient A under predetermined load.

When the electric oscillation output is gradually increased in amplitude by the attenuator 23 from 0 dB, the sense cells E in the root film D of the tooth sense the mechanical oscillation given by the probe 27 to the crown C. When the sensitivity of the sense cells E reaches a threshold value in this manner, the patient A may close the manual switch 10 and thus turn on the pilot lamp or the like in the response display unit 4. Accordingly, a dentist may read the scale on the dial of the attenuator 23 at the time of indication on the display unit 4, and may identify or measure the amplitude of the electric oscillation output corresponding to the threshold value.

Thus, the frequency of the electric oscillation output is sequentially varied, and the threshold value of the output is measured with respect to the amplitude in the same manner as described above for the respective frequencies. Then, the measured results are plotted in a graph, as shown in FIG. 3, in which the frequency (Hz) is represented in an abscissa axis and the amplitude, i.e., the output value (dB) is represented in the ordinate axis, and the degree of the diseased part of the peripheral tissue of the patient's tooth can be relatively compared in the graph for the patient's respective teeth.

By observing the plotted data from the x-axis according to the degree of the diseased part of the environmental tissue of the patient's tooth, there is a threshold value in low frequency and another threshold value in high frequency. According to the experiments, the higher the degree of health of the patient's tooth is, the wider the range of the threshold values thus plotted in the graph, while the lower the degree of health is, the narrower the range of the threshold values in frequency.

It is considered that since a healthy tooth incorporates elastic tension in the environmental tissue of the patient's tooth so that the sensitivity of the sense cells E in the root film D of the patient is high, the cells E may sense frequencies of wide range, while unhealthy or diseased tooth accommodates low elastic tension in the peripheral tissue of the patient's tooth so that the sensitivity of the sense cells E is deteriorated with the result that the frequency range is reduced.

Figure 3:
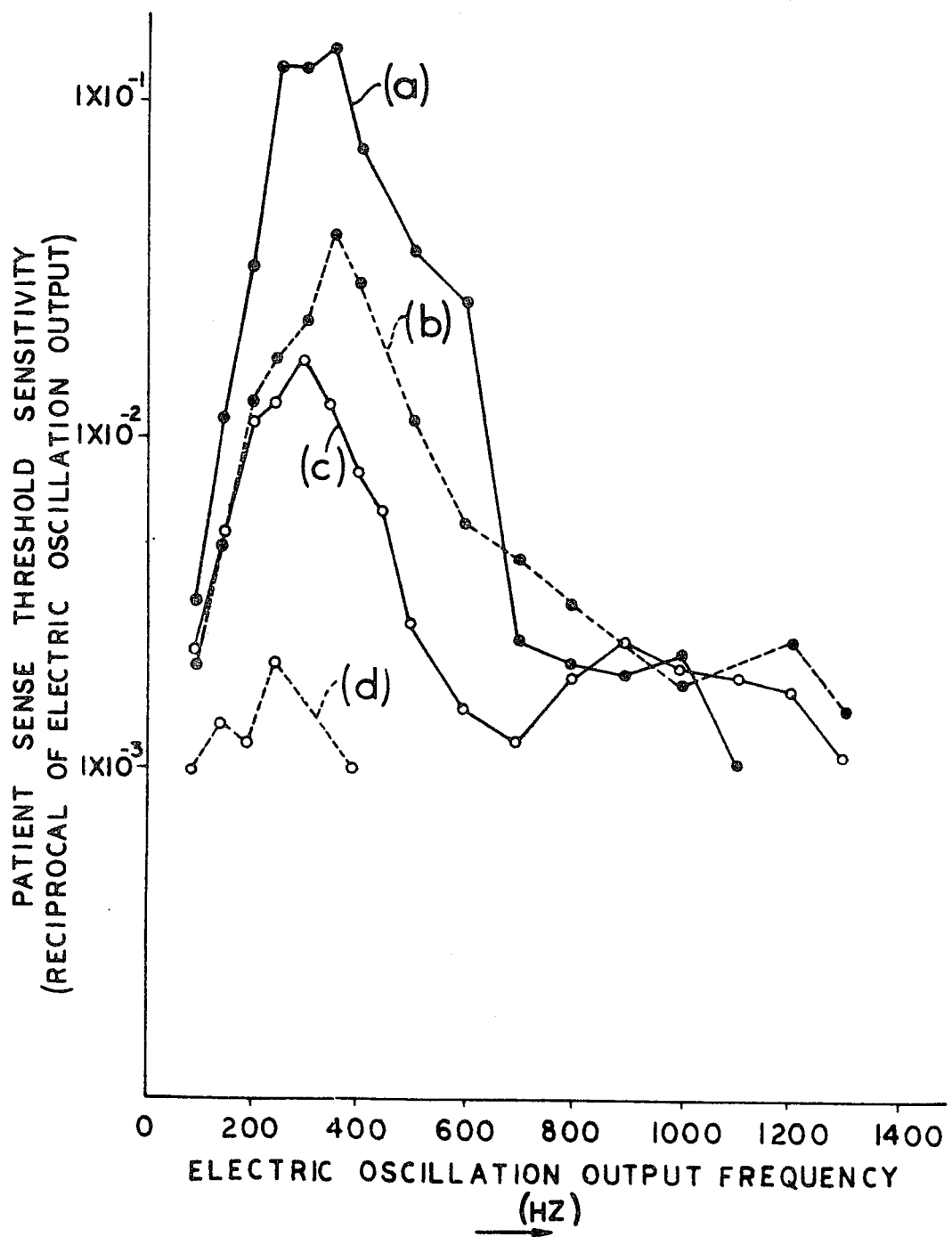
FIG. 3 is a graphical representation of the actually measured results of the relationship between the patient's threshold of sensitivity and the output frequency of an electric oscillation of the apparatus of this invention

When observing the plotted data with respect to the y-axis in the graph shown in FIG. 3, it is also confirmed according to the experiments that the lower the output values (dB) is, the better the degree of health of the patient's tooth is, while the higher the output values (dB) is, the worse the sensitivity of the sense cells E of the patient is.

It is also confirmed according to the experiments that the degree of the diseased part in the environmental tissue of the patient's tooth can be represented by the range of the frequencies and/or the level of the output values, and in case of the output levels, the degree of the diseased part in the peripheral tissue of the patient's tooth can be clearly designated in dB value in the range in frequency of 200 Hz to 600 Hz, and the difference of the output values may be remarkably represented in the vicinity of 300 Hz particularly.

Actually measured results obtained by the experiments are shown in FIG. 3, which proves the aforementioned consideration or concept. The curves are the measured data plotted for patients a, b, c and d with the apparatus of this invention. The patients a and b responded in a considerable, wide range in sensitivity, and actually had better degree of health. On the other hand, the patients c and d responded, as shown, in a narrower range in sensitivity, and actually had considerably more diseased parts in these environmental tissue of the patients. This apparatus had apparently clarified the degree of health of the peripheral tissue of the patient's teeth in wide and various aspects.

When the first switch 14 is connected as designated in FIG. 1 as was already described, the manual interrupter 15 may be opened or closed to arbitrarily interrupt the supply of the electric oscillation output to the electromechanical converter 8. Further, when the first switch 14 is switched, the supply of the electric oscillation output may be interrupted by the automatic interrupter 18 in a predetermined period. When an external electric oscillator is further employed, the second switch 16 may be switched to arbitrarily interrupt the supply of the electric oscillation output. When the supply or transmission of the mechanical oscillation is thus interrupted appropriately to the patient's tooth B, continuous mechanical vibration at the tooth B can be avoided for a long time so as to eliminate paralysis of the patient's sensors so as to obtain highly reliable disgnostic results thereby.

The use of the headphone 12 on the patient A allows high reliability in the diagnostic results by this apparatus by eliminating confusion of external noise on the patient's ear by applying the internal white noise to him.

More particularly, when mechanical oscillation is transmitted from the probe 27 to the tooth B of the patient A, its oscillation sound wave is propagated in the air from the probe 27, and this acoustic oscillation is applied directly to the ear of the patient A. Since the human ear's sensitivity for sounds is generally good, this causes the patient to sense the acoustic oscillation before he senses it as the threshold value through the sense cells E in his root film D, and is thus disturbed in apprehending the correct threshold value.

Accordingly, the headphone 12 shields the external acoustic oscillation from coming into the patient's ear, and serves to transmit the white noise from the electric circuit 6, if this headphone 12 is not enough to shield the external oscillation, so as to paralyze the hearing function of the ear, so that even if the external acoustic oscillation is introduced through the headphone 12 to the patient's ear, it may not adversely affect the sense threshold value measurements at the patient's tooth B.

It should be understood from the foregoing description that the apparatus of this invention operates, as was exemplified in the above embodiment, to supply an electric oscillation output having the desired amplitude at a desired frequency to the electro-mechanical oscillation converter 8. The converter 8 thereupon feeds the mechanical oscillation corresponding to the electric oscillation output from the converter 8 to the probe 27, and allows the patient A to respond when sensing the sense threshold due to the mechanical oscillation from the probe 27 when that the probe 27 is brought into contact with the patient's tooth. The patient responds by operating his responding unit 3, which indicates the frequency and/or the amplitude of the electric oscillation output at the time of patient's response. The dentist or user of this apparatus of the invention can numerically identify the degree of health of the environmental tissue of the patient's tooth without visual examination nor palpation. The sensing frequency band and amplitude of the threshold value are responded to by the patient for the mechanical oscillation transmitted to the tooth to be diagnosed. Later therapy can then proceed in an optimum fashion, and further can exactly diagnose intraperitoneally the diseased part of the patient's tooth.

It should also be appreciated that inasmuch as the apparatus of this invention also incorporates an acoustic sound shielding unit for the patient's ear against external sound transmission, the patient does not confuse the sense threshold felt as a stimulation in sensitivity by mechanical oscillation given to the patient's sense cells with the stimulation of the patient's auditory sensation caused by the sounds of the same frequency transmitted in the environmental air so as to improve further the reliability of this apparatus.

What is claimed is:

1. An apparatus for diagnosing the environmental tissue of teeth comprising:
   means for generating an electric oscillation output having a predetermined characteristic,
   an electro-mechanical oscillation converter connected to said generating means for converting said electric oscillation output into mechanical oscillation,
   an oscillation probe connected to said converter and adapted to be brought into contact with a patient's tooth for applying mechanical oscillation to the tooth,
   means for indicating a response by the patient when he senses the threshold of the mechanical oscillation applied through said probe to his tooth,
   means for measuring the characteristic of the electric oscillation output from said generation circuit at the time of the patient's response, and
   an acoustic sound shielding means for shielding the ear of the patient from external noise conflicting with said mechanical oscillation.

2. The apparatus for diagnosing the environmental tissue of teeth as claimed in claim 1, wherein said acoustic sound shielding means is a headphone to be mounted at the ear of the patient, an electric circuit for generating white noise conflicting with noise generated by said mechanical oscillation applied to the patient's tooth, and means for connecting said white noise generating circuit to said headphone.

* * * * *